United States Patent
Nishii et al.

(10) Patent No.: US 7,868,107 B2
(45) Date of Patent: Jan. 11, 2011

(54) PROCESS FOR PRODUCING CYCLOOLEFIN ADDITION POLYMER, CATALYST FOR ADDITION POLYMERIZATION OF CYCLOOLEFIN, AND TRANSITION METAL COMPOUND

(75) Inventors: Kei Nishii, Tokyo (JP); Sigetaka Hayano, Tokyo (JP); Yasuo Tsunogae, Tokyo (JP)

(73) Assignee: Zeon Corporation, Tokyo (JP)

(*) Notice: Subject to any disclaimer, the term of this patent is extended or adjusted under 35 U.S.C. 154(b) by 376 days.

(21) Appl. No.: 12/073,704

(22) Filed: Mar. 7, 2008

(65) Prior Publication Data
US 2009/0124769 A1 May 14, 2009

Related U.S. Application Data

(60) Provisional application No. 60/914,851, filed on Apr. 30, 2007.

(30) Foreign Application Priority Data

Mar. 9, 2007 (JP) .............................. 2007-061065

(51) Int. Cl.
C08F 4/64 (2006.01)
C08F 4/642 (2006.01)
C08F 4/643 (2006.01)
C08F 4/6592 (2006.01)

(52) U.S. Cl. ................. 526/161; 526/133; 526/134; 526/160; 526/165; 526/308; 526/943

(58) Field of Classification Search ................. 526/133, 526/134, 160, 161, 165, 308, 943
See application file for complete search history.

(56) References Cited

U.S. PATENT DOCUMENTS 6,310,164 B1 * 10/2001 Morizono et al. ............ 526/339
6,348,555 B1 * 2/2002 Lai et al. ...................... 526/336

* cited by examiner

Primary Examiner—Caixia Lu
(74) Attorney, Agent, or Firm—Birch, Stewart, Kolasch & Birch, LLP

(57) ABSTRACT

A process for producing a cycloolefin addition polymer comprising addition-polymerizing a cycloolefin in the presence of a catalyst comprising a combination of a specific transition metal compound of Group 4 of the Periodic Table, with an organoaluminum oxy compound, and/or a compound capable of reacting with the Group 4 transition metal compound to form an ion pair. The specific group 4 transition metal compound preferably has a structure such that the group 4 transition metal is bonded to a cyclopentadienyl ring in an $\eta^1$ mode. The above-mentioned catalyst exhibits high activity for both of addition homopolymerization of a cycloolefin and addition copolymerization of a cycloolefin with an $\alpha$-olefin.

11 Claims, 2 Drawing Sheets

PROCESS FOR PRODUCING CYCLOOLEFIN ADDITION POLYMER, CATALYST FOR ADDITION POLYMERIZATION OF CYCLOOLEFIN, AND TRANSITION METAL COMPOUND

TECHNICAL FIELD

This invention relates to a novel process for producing a cycloolefin addition polymer, and a catalyst used therefor, and a transition metal compound.

The catalyst according to the present invention is characterized as exhibiting a high activity for both of addition polymerization of a cycloolefin and addition copolymerization of a cycloolefin with an α-olefin.

BACKGROUND ART

It is known that an addition polymer of a cycloolefin such as norbornene or tetracyclododecene, and an addition copolymer of a cycloolefin such as norbornene or tetracyclododecene with an α-olefin such as ethylene or propylene have high heat resistance, high transparency, low water absorbance, low refractive index and good electrical properties, and therefore, the addition polymers and copolymers are suitable for optical parts such as optical lens, optical memory disc, optical fiber and optical film, and electronic and electrical parts such as electrically insulating part.

In recent years, many proposals have been made with regard to a catalyst used for the production of the addition polymers and copolymers, and a process for producing the addition polymers and copolymers. For example, nickel catalysts and palladium catalysts have been proposed as a catalyst for addition polymerization of a cycloolefin in Japanese Patent Publication (hereinafter referred to as "JP-A") No. H09-508649 and International Publication No. WO00/20472. Metallocene catalysts and post-metallocene catalysts have been proposed as a catalyst for addition copolymerization of a cycloolefin with an α-olefin in JP-A H03-45612 and JP-A 2004-331966.

However, the nickel catalysts and palladium catalysts proposed in JP-A H09-508649 and WO00/20472 exhibit a high activity for the addition polymerization of a cycloolefin, but, they do not exhibit at all an activity for the addition copolymerization of a cycloolefin with an α-olefin. The metallocene catalysts and post-metallocene catalysts, proposed in JP-A H03-45612 and JP-A 2004-331966, exhibit a high activity for the addition copolymerization of a cycloolefin with an α-olefin, but, they exhibit a poor activity for the addition polymerization of a cycloolefin. Therefore, a catalyst capable of exhibiting a high activity for both of the addition polymerization of a cycloolefin and the addition copolymerization of a cycloolefin with an α-olefin has been desired.

In view of the foregoing, a CGC type metallocene catalyst having a fluorenyl group has been proposed as a catalyst capable of exhibiting an activity for both of the addition polymerization of norbornene and the addition copolymerization of norbornene with ethylene in JP-A 2004-107442. The catalytic activity is described as relatively high in this patent publication, but, the catalytic activity is not to a sufficient extent from an industrial viewpoint.

It is described in Journal of the American Chemical Society, vol. 126, pp 16716-16717, 2004, that, in a CGC type metallocene complex having a substituted fluorenyl group, a transition metal is bonded to the substituted fluorenyl group in an $\eta^1$ mode; and further that a catalyst comprised of this CGC type metallocene complex exhibits a high activity especially for polymerization of a long-chain α-olefin. However, the catalytic activity of this CGC type metallocene complex catalyst for a cycloolefin is not known.

A complex comprising a group 4 transition metal atom having coordinated thereto a neutral Lewis base is described in claim 1 of JP-A H05-507756. However, any specific example of this complex is not mentioned in this patent publication. In this patent publication, only a compound having a substituted cyclopentadienyl group bonded to a group 4 transition metal compound in an $\eta^5$ mode is specifically described as a group 4 transition metal compound constituting the above-mentioned complex.

DISCLOSURE OF THE INVENTION

In view of the foregoing prior art, a primary object of the present invention is to provide a polymerization catalyst capable of exhibiting a high activity for both of the addition polymerization of a cycloolefin and the addition copolymerization of a cycloolefin with an α-olefin. Another object thereof is to provide a process for polymerization using the above-mentioned catalyst.

The present inventors made extensive research to achieve the above-mentioned objects, and found that a transition metal complex having a substituted cyclopentadienyl group bonded to a group 4 transition metal atom in an $\eta^1$ mode has a large space between the substituted cyclopentadienyl group and the transition metal whereby a neutral Lewis base can be coordinated; and further that a polymerization catalyst comprising a combination of this transition metal complex with aluminoxane or a borate exhibits a very high polymerization activity for both of polymerization of bulky olefins such as cycloolefins and 1-hexene, and polymerization of relatively small olefins such as ethylene and propylene, and consequently, a very high polymerization activity for both of addition polymerization of a cycloolefin and addition copolymerization of a cycloolefin with an α-olefin. Based on these findings, the present invention has been completed.

Thus, in one aspect of the present invention, there is provided a process for producing a cycloolefin addition polymer comprising addition-polymerizing a cycloolefin in the presence of a catalyst comprising a combination of (A) a transition metal compound of Group 4 of the Periodic Table, represented by the following general formula (1), with (B) an organoaluminum oxy compound, and/or (C) a compound capable of reacting with the Group 4 transition metal compound (A) to form an ion pair,

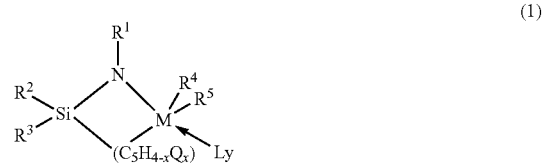

(1)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $C_5H_{4-x}Q_x$ refers to a cyclopentadienyl ring having "x" number of substituents Q, where x is an integer of 1 to 4, and each Q independently represents a $C_1$-$C_{20}$ hydrocarbon group which may have a halogen atom or atoms as a substituent, or a silyl group which may have a $C_1$-$C_{12}$ hydrocarbon group or groups as a substituent; wherein two adjacent Qs in the $C_5H_{4-x}Q_x$ may be bonded, together with the carbon atoms to which the two Qs are attached, to form a cyclic moiety having 4 to 20 carbon atoms whereby the $C_5H_{4-x}Q_x$ is rendered a polycyclic cyclopentadienyl ring; L is a neutral Lewis base, and y is an integer of 1 or 2.

In another aspect of the present invention, there is provided a catalyst for addition-polymerization of a cycloolefin comprising a combination of (A) a transition metal compound of Group 4 of the Periodic Table, represented by the above-mentioned general formula (1), with (B) an organoaluminum oxy compound, and/or (C) a compound capable of reacting with the Group-4 transition metal compound (A) to form an ion pair.

In a further aspect of the present invention, there is provided a transition metal compound of Group 4 of the Periodic Table, represented by the following general formula (3):

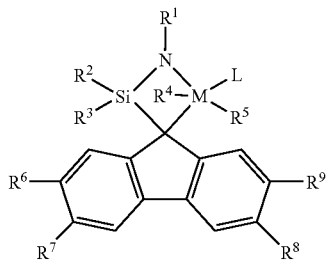

(3)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $R^6$ to $R^9$ each independently represent a hydrogen atom, a $C_1$-$C_{12}$ alkyl group, a $C_5$-$C_{12}$ cycloalkyl group, a $C_6$-$C_{12}$ aryl group or a halogen atom, or a $C_1$-$C_{12}$ hydrocarbon group which may have a halogen atom or atoms as a substituted, or a silyl group which may have a $C_1$-$C_{12}$ hydrocarbon group or groups as a substituent, provided that, in the case when M is titanium, $R^6$ and $R^7$, and/or $R^8$ and $R^9$ may be bonded together to form a ring; and L is a neutral Lewis base.

According to the present invention, an addition polymer of a cycloolefin, and an addition copolymer of a cycloolefin with an α-olefin with a copolymerization ratio of cycloolefin in a broad range of 1% by mole to 100% by mole, can be obtained with an enhanced efficiency.

DETAILED DESCRIPTION OF THE INVENTION

Group 4 Transition Metal Compound (A)

Figures 1, 2:
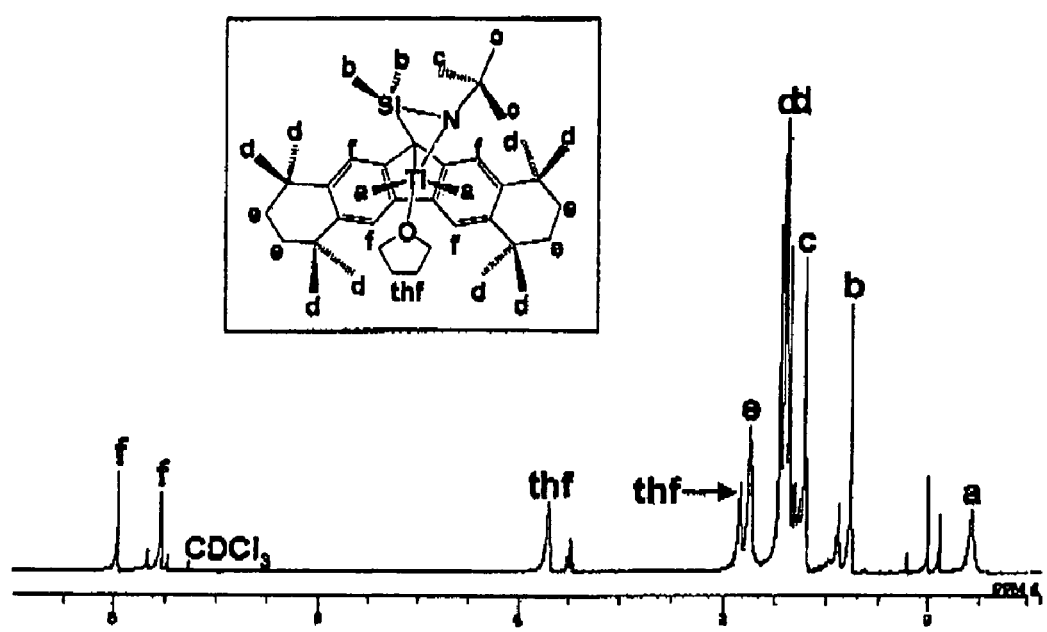
FIG. 1 is a H-NMR spectrum of complex I obtained in Example 1.
FIG. 2 is an illustration of X-ray structure analysis of complex I obtained in Example 1 (ORTEP [Oak Ridge Thermal Ellipsoid Plot]; hydrogen atoms are not shown).

The catalyst used for the production of a cycloolefin addition polymer according to the present invention comprises a combination of (A) a transition metal compound of Group 4 of the Periodic Table (hereinafter referred to as "transition metal compound (A)" when appropriate), represented by the following general formula (1), with (B) an organoaluminum oxy compound, and/or (C) a compound capable of reacting with the transition metal compound (A) to form an ion pair.

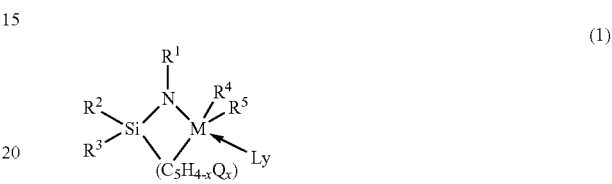

(1)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_5$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $C_5H_{4-x}Q_x$ refers to a cyclopentadienyl ring having "x" number of substituents Q, where x is an integer of 1 to 4, and each Q independently represents a $C_1$-$C_{20}$ hydrocarbon group which may have a halogen atom or atoms as a substituent, or a silyl group which may have a $C_1$-$C_{12}$ hydrocarbon group or groups as a substituent; wherein two adjacent Qs in the $C_5H_{4-x}Q_x$ may be bonded, together with the carbon atoms to which the two Qs are attached, to form a cyclic moiety having 4 to 20 carbon atoms whereby the $C_5H_{4-x}Q_x$ is rendered a polycyclic cyclopentadienyl ring; L is a neutral Lewis base, and y is an integer of 1 or 2.

In the transition metal compound (A) of the general formula (1), M represents a transition metal atom of Group 4 of the Periodic Table, which includes titanium, zirconium and hafnium. Of these, titanium and zirconium are preferable. Titanium is especially preferable.

$R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group. As specific examples of $R^1$ to $R^3$, there can be mentioned alkyl groups such as methyl, ethyl, propyl, isopropyl, butyl, isobutyl, t-butyl, pentyl, hexyl, heptyl and octyl groups; cycloalkyl groups such as cyclopentyl, cyclohexyl and adamantyl groups; and aryl groups such as phenyl, biphenyl and naphthyl groups. The alkyl, cycloalkyl and aryl groups may have a halogen atom or atoms as a substituent. The cycloalkyl and aryl groups may have the aforementioned alkyl group or groups as a substituent.

$R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom. As specific examples of $R^4$ and $R^5$, there can be mentioned halogen atoms such as fluorine, chlorine, iodine and bromine atoms; alkyl groups such as methyl, ethyl, propyl, isopropyl, butyl, isobutyl, t-butyl, pentyl, hexyl, heptyl and octyl groups; cycloalkyl groups such as cyclopentyl, cyclohexyl and adamantyl groups; and aryl groups such as phenyl, biphenyl and naphthyl groups. The alkyl, cycloalkyl and aryl groups may have a halogen atom or atoms as a substitutent. The cycloalkyl and aryl groups may have the aforementioned alkyl group or groups as a substituent.

$C_5H_{4-x}Q_x$ refers to a cyclopentadienyl ring having "x" number of substituents Q. x is an integer of 1 to 4. Each Q independently represents a $C_1$-$C_{20}$ hydrocarbon group which may have a halogen atom or atoms as a substituent, or a silyl group which may have a $C_1$-$C_{12}$ hydrocarbon group or groups as a substituent. As specific examples of Q, there can be mentioned alkyl groups such as methyl, ethyl, propyl, isopropyl, butyl, isobutyl, t-butyl, pentyl, hexyl, heptyl and octyl groups, which may have a halogen atom or atoms as a substituent; cycloalkyl groups such as cyclopentyl and cyclohexyl groups, which may have a halogen atom or atoms as a substituent; and aryl groups such as phenyl, biphenyl and naphthyl groups, which may have a halogen atom or atoms as a substituent; and silyl groups which may have a $C_1$-$C_{12}$ hydrocarbon group or groups as a substituent, wherein the hydrocarbon group includes, for example, alkyl groups such as methyl, ethyl, propyl, isopropyl, butyl, isobutyl, t-butyl, pentyl, hexyl, heptyl and octyl groups, which may have a halogen atom or atoms as a substituent, and cycloalkyl groups such as cyclopentyl and cyclohexyl groups, which may have a halogen atom or atoms as a substituent.

The above-mentioned alkyl groups and aryl groups may have an alkyl group or groups, as a substituent, such as those which are recited above.

Two adjacent Qs in the $C_5H_{4-x}Q_x$ may be bonded to form a cyclic moiety having 4 to 20 carbon atoms together with the carbon atoms to which the two Qs are attached in the cyclopentadienyl ring whereby the $C_5H_{4-x}Q_x$ is rendered a polycyclic cyclopentadienyl ring. Such polycyclic cyclopentadienyl ring includes, for example, indenyl, tetrahydroindenyl and fluorenyl groups. These groups may have a substituent such as the above-mentioned alkyl and aryl groups, and further may be bonded with a fused ring.

L is a neutral Lewis base, and y is an integer of 1 or 2. In the case when the substituted cyclopentadienyl group $C_5H_{4-x}Q_x$ in the transition metal compound (A) is bonded to M in an $\eta^1$ mode, the neutral Lewis base L can easily be coordinated. As specific examples of the neutral Lewis base, there can be mentioned ethers such as diethyl ether and tetrahydrofuran; amines such as dimethylaniline and triethylamine; pyridines such as pyridine and methylpyridine; nitriles such as acetonitrile and benzonitrile; esters such as methyl acetate and ethyl acetate; phosphines such as trimethylphosphine and triphenylphosphine; thioethers such as phenylethyl thioether; and amides such as dimethylacetamide. Of these, ethers, pyridines, phosphines and nitrites are preferable. Ethers are especially preferable.

In the transition metal compound (A) used in the present invention, the substituted cyclopentadienyl group is bonded to the central transition metal M preferably in an $\eta^1$ mode. The $\eta^1$ mode bonding can be confirmed by determine the bond distance between the central transition metal and each of the five carbon atoms on the substituted pentadienyl ring by X-ray structural analysis.

When the substituted cyclopentadienyl group is bonded to the central transition metal M in an $\eta^1$ mode, there is a space between the substituted cyclopentadienyl group and the central transition metal M, and thus, the neutral Lewis base can easily be coordinated. The transition metal compound (A) according to the present invention can be characterized as having the coordinated neutral Lewis base. The coordination of the neutral Lewis base can be determined by elementary composition analysis, NMR spectroscopic analysis or X-ray crystal structure analysis.

A preferable example of the transition metal compound (A) represented by the formula (1) is a transition metal compound represented by the following general formula (3).

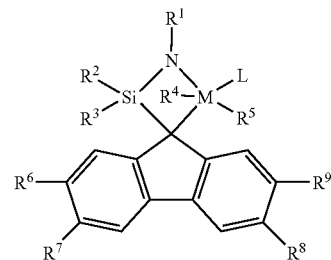

(3)

wherein $R^1$ to $R^9$, M and L are the same as defined with regard to the general formula (3) hereinbefore shown.

AS specific examples of the $R^1$ to $R^5$ in the general formula (5), there can be mentioned those which are recited for $R^1$ to $R^5$ in the general formula (1) hereinbefore shown. As specific examples of $R^6$ to $R^9$, there can be mentioned those which are recited for $R^4$ and $R^5$ in the general formula (1).

The transition metal M is preferably selected from titanium and zirconium. $R^1$ is preferably selected from t-butyl, adamantly and phenyl groups. $R^2$ and $R^3$ are preferably selected from methyl and phenyl groups. $R^4$ and $R^5$ are preferably selected from chlorine atom, bromine atom, methyl group and phenyl group. L is preferably selected from diethyl ether and tetrahydrofuran. $R^6$ to $R^9$ are preferably selected from hydrogen atom and $C_1$-$C_{12}$ alkyl groups.

The compounds represented by the general formula (3) are novel except for compounds wherein M is zirconium or hafnium, and $R^6$ and $R^7$, and/or $R^8$ and $R^9$ may be bonded together to form a ring.

Of the compounds represented by the general formula (3), titanium compounds represented by the following general formula (2) are especially preferable because these titanium compounds exhibit high polymerization activity for both of the addition polymerization of a cycloolefin and the addition copolymerization of a cycloolefin with an α-olefin.

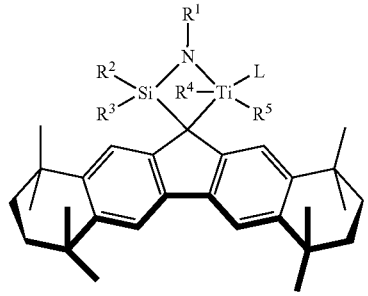

(2)

wherein $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; and L is a neutral Lewis base.

As specific examples of $R^1$ to $R^5$ and L in the general formula (2), there can be mentioned those which are recited with regard to the general formula (1) hereinbefore shown.

The transition metal compound (A) represented by the general formula (1) can be synthesized by known synthesizing methods, which include, for example, the methods described in:

(1) Journal of the American Chemical Society, vol. 126, pp 16716-16717 (2004), and Macromolecules, vol. 31, No. 10, pp 3184-3188 (1998); and (2) Metalorganic Catalysts for Synthesis and Polymerization, edited by W. Kaminsky, published by Springer-Varlag (Berlin), pp 264-273 (1999).

Organic Aluminum Oxy Compound (B), and Compound (C) Capable of Reacting with Group 4 Transition Metal Compound (A) to Form Ion Pair The compound (B) and the compound (C) have a function of activating the transition metal compound (A). The compound (B), and the compound (C) capable of reacting with the transition metal compound (A) to form an ion pair, may be used either alone or as a combination of at least two thereof.

The organic aluminum oxy compound (B) includes conventional aluminoxanes, and benzene-insoluble organic aluminum oxy compounds described in JP-A H02-78687.

Aluminoxanes are products obtainable by the reaction of a trialkylaluminum with water. The aluminoxanes include, for example, methylaluminoxane, ethylaluminoxane, propylaluminoxane, butylaluminoxane, isobutylaluminoxane, methylethylaluminoxane, methylbutylaluminoxane and methylisobutylaluminoxane. These aluminoxanes may be used either alone or as a combination of at least two thereof. Of these, methylaluminoxane is preferable.

The compound (C) capable of reacting with the transition metal compound (A) to form an ion pair includes, for example, Lewis acids, ionic compounds, borane compounds and carborane compounds. These compounds are described in JP-A H1-501950, JP-A H1-502036, JP-A H3-179005, JP-A H3-179006, JP-A H3-207703, JP-A H3-207704 and U.S. Pat. No. 5,321,106. Further, the compounds (C) includes heteropoly compounds and isopoly compounds.

More specifically, the Lewis acids include compounds represented by the formula $BR^6_3$, wherein $R^6$ independently represents a fluorine atom, a phenyl group, or a phenyl group having as a substituent a fluorine atom or fluorine-substituted alkyl group. As specific examples thereof, there can be mentioned trifluoroboron, triphenylboron, tris(4-fluorophenyl) boron, tris(3,5-difluorophenyl)boron, tris(4-fluoromethylphenyl)boron and tris(pentafluorophenyl)boron.

The ionic compounds include, for example, borate salts and aluminate salts.

As specific examples of the borate salts, there can be mentioned lithium tetrakis(2-fluorophenyl)borate, sodium tetrakis(3-fluorophenyl)borate, silver tetrakis(pentafluorophenyl)borate, thallium tetrakis(4-fluorophenyl)borate, ferrocenium (3,5-difluorophenyl)borate, trityl tetrakis(3,4,5-trifluorophenyl)borate, sodium tetrakis[3,5-bis(trifluoromethyl)phenyl]borate, N,N-dimethylanilinium tetrakis(2,3,4,5-tetrafluorophenyl)borate, triethylsilylium tetrakis(pentafluorophenyl)borate, triphenylsilylium tetrakis(pentafluorophenyl)borate, lithium tetrakis[tris(trifluoromethyl)methoxy]borate, thallium tetrakis-[1,1-bis(trifluoromethyl)ethoxy]borate, trityl tetrakis-[bis(trifluoromethyl)methoxy]borate, silver [1,1-bis(trifluoromethyl)ethoxy]borate, lithium bis(tetrafluorocatechol)borate, [silver(toluene)₂]bis(tetrafluorocatechol)borate and thallium bis(tetrachlorocatechol)borate.

As specific examples of the aluminate salts, there can be mentioned lithium tetrakis(pentafluorophenyl)aluminate, trityl tetrakis(pentafluorophenyl)aluminate, trityl (perfluorobiphenyl)fluoroaluminate, sodium tetrakis[3,5-bis(trifluoromethyl)phenyl]aluminate, potassium (octyloxy)tris(pentafluorophenyl)aluminate, magnesium terakis(pentafluorophenyl)aluminate, calcium terakis(pentafluorophenyl)aluminate, lithium terakis(bis(trifluoromethyl)phenylmethoxy)aluminate, thallium terakis-[1,1-bis(trifluoromethyl)ethoxy]aluminate, trityl terakis-[bis(trifluoromethyl)methoxy]aluminate, silver terakis[1,1-bis(trifluoromethyl)ethoxy]aluminate, lithium bis(tetrafluorocatechol)aluminate and lithium terakis-[bis(trifluoromethyl)-4-isopropylphenylmethoxy]aluminate.

If desired, an organoaluminum compound (D) can be used in combination with the catalyst according to the present invention. The organoaluminum compound (D) includes, for example, those which are represented by the following general formula (4):

$$(R^{10})_z AlX_{3-z} \qquad (4)$$

wherein $R^{10}$ represents a $C_1$-$C_{15}$ hydrocarbon group, preferably a $C_1$-$C_8$ hydrocarbon group, X represents a halogen atom or a hydrogen atom, and z is an integer of 1 to 3.

As specific examples of the $C_1$-$C_{15}$ hydrocarbon group, there can be mentioned alkyl groups such as methyl, ethyl, n-propyl, isopropyl, isobutyl and n-octyl groups; cycloalkyl groups; and aryl groups.

As specific examples of the organoaluminum compound, there can be mentioned trialkylaluminums such as trimethylaluminum, triethylaluminum, triisopropylaluminum, tri-n-butylaluminum, triisobutylaluminum and tri-sec-butylaluminum; alkenylaluminums such as isoprenylaluminum represented by the following general formula:

$$(i\text{-}C_4H_9)_p Al_q (C_5H_{10})_r$$

wherein p, q and r are positive numbers, and r.gtoreq.2p; dialkylaluminum halides such as dimethylaluminum chloride and diisobutylaluminum chloride; dialkylaluminum hydrides such as diisobutylaluminum hydride; dialkylaluminum alkoxides such as dimethylaluminum methoxide; and dialkylaluminum aryloxides such as diethylaluminum phenoxide.

In the present invention, the ratio in amount of the transition metal compound (A) to the organic aluminum oxy compound (B) or the compound (C) capable of reacting with the transition metal compound (A) to form an ion pair, or to the organoaluminum compound (D) are appropriately chosen.

The ratio in amount of the transition metal compound (A) to the organic aluminum oxy compound (B) is usually in the range of 1/0.1 to 1/10,000, preferably 1/0.5 to 1/5,000 and more preferably 1/1 to 1/2,000 as expressed by the mole ratio of the transition metal in the compound (A) to the aluminum atom in the compound (B).

The ratio in amount of the transition metal compound (A) to the compound (C) capable of reacting with the compound (A) to form an ion pair is usually in the range of 1/0.1 to 1/100, preferably 1/0.5 to 1/50 and more preferably 1/1 to 1/20 as expressed by mole ratio.

In the case when the organoaluminum compound (D) is used, the ratio in amount of the transition metal compound (A) to the organoaluminum compound (D) is usually in the range of 1/0.1 to 1/0.100, preferably 1/0.5 to 1/50 and more preferably 1/1 to 1/20 as expressed by mole ratio (A)/(D).

The mixing of the above-mentioned catalyst ingredients can be carried out in a solvent. The solvent is not particularly limited, but, an inert, commercially readily available solvent is preferably used.

As specific examples of the solvent, there can be mentioned aliphatic hydrocarbons such as pentane, hexane and heptane; alicyclic hydrocarbons such as cyclopentane, cyclohexane, methylcyclohexane, dimethylcyclohexane, trimethylcyclohexane, ethylcyclohexane, diethylcyclohexane, decahydronaphthalene, bicycloheptane, tricyclodecane, hexahydroindene and cyclooctane; aromatic hydrocarbons such as benzene, toluene and xylene; nitrogen-containing solvents such as nitromethane, nitrobenzene and acetonitrile; ethers such as diethyl ether and tetrahydrofuran; and halogenated solvents such as dichloromethane, chloroform, chlorobenzene and dichlorobenzene. Of these, aromatic hydrocarbons, aliphatic hydrocarbons, alicyclic hydrocarbons, ethers and halogenated solvents are preferable.

The temperature at which the catalyst ingredients are mixed together is not particularly limited, but the temperature is usually in the range of −200° C. to 200° C., preferably −150° C. to 150° C. and more preferably −100° C. to 100° C.

Process for Producing Cycloolefin Addition Polymer

The process for producing a cycloolefin addition polymer according to the present invention comprises polymerizing a monomer containing a cycloolefin in the presence of the above-mentioned polymerization catalyst.

The cycloolefin preferably includes norbornene compound monomers represented by the following general formula (5).

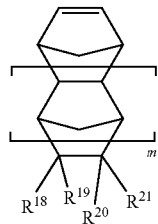

(5)

wherein $R^{18}$ to $R^{21}$ independently represent a hydrogen atom, a halogen atom or a hydrocarbon group.

The halogen atom includes fluorine, chlorine, bromine and iodine atoms.

The hydrocarbon group includes, for example, a $C_1$-$C_{20}$ alkyl group, a $C_2$-$C_{20}$ alkenyl group, a $C_3$-$C_{20}$ cycloalkyl group, a $C_3$-$C_{20}$ cycloalkenyl group, and a $C_6$-$C_{20}$ aromatic hydrocarbon group. These hydrocarbon groups may be partly substituted by a halogen atom or atoms, or may be partly substituted by a polar group or groups other than the halogen atom or atoms.

As specific examples of the $C_1$-$C_{20}$ alkyl group, there can be mentioned methyl, ethyl, propyl, isopropyl, amyl, hexyl, octyl, decyl and dodecyl groups. As specific examples of the $C_2$-$C_{20}$ alkenyl group, there can be mentioned propenyl, isopropepyl, butenyl, isobutenyl, pentenyl and hexenyl groups. As specific examples of the $C_3$-$C_{20}$ cycloalkyl group, there can be mentioned cyclopentyl and cyclohexyl groups. As specific examples of the $C_3$-$C_{20}$ cycloalkenyl group, there can be mentioned cyclopentenyl and cyclohexenyl groups. As specific examples of the aromatic hydrocarbon group, there can be mentioned phenyl and naphthyl groups.

$R^{19}$ and $R^{20}$ may be bonded together to form a single ring or a condensed ring. The single ring or a condensed ring may have a double bond.

The single ring formed from $R^{19}$ and $R^{20}$ includes cyclopentane, cyclopentene, cyclohexane, cyclohexene and benzene rings. The condensed ring formed from $R^{19}$ and $R^{20}$ includes those which are a combination of each of these single rings with other ring structure.

$R^{18}$ and $R^{19}$ and/or $R^{20}$ and $R^{21}$ may form together an alkylidene group. As specific examples of the alkylidene group, there can be mentioned methylidene, ethylidene, propylidene and isopropylidene groups.

m in the general formula (5) is an integer of 0 to 2. In the case when m is 0, the norbornene compound monomer is a norbornene monomer. In the case when m is 1, the norbornene compound monomer is a tetracyclododecene monomer.

The norbornene monomer with m of 0 includes unsubstituted norbornene monomers and substituted norbornene monomers, and, as specific examples thereof, there can be mentioned 2-norbornene; norbornene monomers having a halogen atom such as 5-chloro-2-norbornene; norbornene monomers having an alkyl group such as 5-methyl-2-norbornene, 5-ethyl-2-norbornene, 5-butyl-2-norbornene, 5-hexyl-2-norbornene and 5-decyl-2-norbornene; norbornene monomers having an alkenyl group such as 5-vinyl-2-norbornene and 5-propenyl-2-norbornene; norbornene monomers having a cycloalkyl group such as 5-cyclohexyl-2-norbornene and 5-cyclopentyl-2-norbornene; norbornene monomers having a cycloalkenyl group such as 5-cyclopentenyl-2-norbornene and 5-cyclohexenyl-2-norbornene; norbornene monomers having an aromatic hydrocarbon group such as 5-phenyl-2-norbornene, p-methyl-5-phenyl-2-norbornene, o-methyl-5-phenyl-2-norbornene and m-methyl-5-phenyl-2-norbornene; and norbornene monomers having a hydrocarbon group with a halogen atom as a substituent such as 5-chloromethyl-2-norbornene and p-chloro-5-phenyl-2-norbornene.

As specific examples of the norbornene compound monomers of the general formula (5) wherein $R^{19}$ and $R^{20}$ are bonded together to form a single ring or a condensed ring, there can be mentioned dicyclopentadiene, methyldicyclopentadiene, dihydrodicyclopentadiene (tricyclo[5.2.1.0$^{2,6}$] deca-8-ene), tetracyclo[9.2.1.0$^{2,10}$.0$^{3,8}$]tetradeca-3,5,7,12-teraene (1,4-methano-1,4,4a,9a-tetrahydro-9H-fluorene) and tetracyclo[10.2.1.0$^{2,10}$.0$^{4,9}$]pentadeca-4,6,8,13-teraene (i.e., 1,4-methano-1,4,4a,9,9a,10-hexahydroanthracene).

As specific examples of the norbornene compound monomers of the general formula (5) wherein $R^{18}$ and $R^{19}$, and/or $R^{20}$ and $R^{21}$ form together an alkylidene group, there can be mentioned 5-methylidene-2-norbornene, 5-ethylidene-2-norbornene, 5-propylidene-2-norbornene and 5-isopropylidene-2-norbornene.

As specific examples of the tetracyclodocene monomers with m of 1, there can be mentioned tetracyclo[6.2.1.1$^{3,6}$.0$^{2,7}$]dodeca-4-ene; tetracyclododecene monomers having a halogen atom such as 9-chlorotetracyclo[6.2.1.1$^{3,6}$.0$^{2,7}$] dodeca-4-ene and 9-bromotetracyclo[6.2.1.1$^{3,6}$.0$^{2,7}$]dodeca-4-ene; tetracyclododecene monomers having an alkyl group such as 9-methyltetracyclo[6.2.1.1$^{3,6}$.0$^{2,7}$]dodeca-4-ene, 9-ethyltetracyclo[6.2.1.1$^{3,6}$.0$^{2,7}$]dodeca-4-ene, 9-butyltetracyclo[6.2.1.1$^{3,6}$.0$^{2,7}$]dodeca-4-ene, 9-hexyltetracyclo [6.2.1.1$^{3,6}$.0$^{2,7}$]dodeca-4-ene and 9-decyltetracyclo[6.2.1. 1$^{3,6}$.0$^{2,7}$]dodeca-4-ene; tetracyclododecene monomers having an alkenyl group such as 9-vinyltetracyclo[6.2.1.1$^{3,6}$. 0$^{2,7}$]dodeca-4-ene and 9-propenyltetracyclo[6.2.1.1$^{3,6}$.0$^{2,7}$] dodeca-4-ene; tetracyclododecene monomers having a cycloalkyl group such as 9-cyclohexyltetracyclo[6.2.1. 1$^{3,6}$.0$^{2,7}$]dodeca-4-ene and cyclopentyltetracyclo[6.2.1. 1$^{3,6}$.0$^{2,7}$]dodeca-4-ene; tetracyclododecene monomers having a cycloalkenyl group such as 9-cyclopentenyltetracyclo [6.2.1.1$^{3,6}$.0$^{2,7}$]dodeca-4-ene and 9-cyclohexenyltetracyclo [6.2.1.1$^{3,6}$.0$^{2,7}$]dodeca-4-ene; tetracyclododecene monomers having an aromatic hydrocarbon group such as 9-phenyltetracyclo[6.2.1.1$^{3,6}$.0$^{2,7}$]dodeca-4-ene; and tetracyclododecene monomers having a hydrocarbon group with a halogen atom as a substituent such as 9-chloromethyltetracyclo[6.2.1.1$^{3,6}$.0$^{2,7}$]dodeca-4-ene.

The norbornene compound monomers of the general formula (5) wherein $R^{18}$ and $R^{19}$, and/or $R^{20}$ and $R^{21}$ form together an alkylidene group, further includes, for example, 9-methylidenetetracyclo[6.2.1.1$^{3,6}$.0$^{2,7}$]dodeca-4-ene and 9-ethylidenetetracyclo[6.2.1.1$^{3,6}$.0$^{2,7}$]dodeca-4-ene.

In the case when the cycloolefin addition polymer produced by the process according to the present invention is used as a material for shaping into optical goods, the norbornene compound monomers of the general formula (5) are preferably those in which $R^{18}$ to $R^{21}$ are selected from a hydrogen atom, and $C_1$-$C_{20}$ alkyl, $C_3$-$C_{20}$ cycloalkyl group, and $C_6$-$C_{20}$ aromatic hydrocarbon groups, in view of the shapability, transparency and heat-resistance. $R^{18}$ to $R^{21}$ are especially preferably a hydrogen atom.

The process for producing the cycloolefin addition polymer includes not only addition polymerization of the above-mentioned cycloolefin but also addition copolymerization of the cycloolefin with a copolymerizable monomer or monomers. The copolymerizable monomer includes, for example, $C_2$-$C_{20}$ α-olefins, and, as specific examples thereof, there can be mentioned ethylene, propylene, 1-butene, 1-pentene, 3-methyl-1-butene, 1-hexene, 3-methyl-1-pentene, 4-methyl-1-pentene, 1-heptene, 1-octene, vinylcyclohexane, 1-nonene, 3-cyclohexyl-1-propene, 1-decene, 1-undecene and 1-dodecene.

The polymerization catalyst of the present invention exhibits improved activity for polymerization of long chain α-olefins such as 1-hexene and 1-octene, as well as short chain α-olefins such as ethylene and propylene. Thus, the polymerization catalyst exhibits enhanced activity for copolymerization of a cycloolfin with various, optional α-olefins.

The monomer copolymerizable with the cycloolefin further includes, for example, styrenic monomers such as styrene, α-methylstyrene, p-methylstyrene, p-chlorostyrene and indene; and chainlike conjugated diene monomers such as 1,3-butadiene and isoprene.

The ratio of the catalyst to the monomer or monomers is such that the ratio by mole of the transition metal atom in the transition metal compound (A) to the monomer or monomers is usually in the range of 1/100 to 1/2,000,000, preferably 1/200 to 1/1,000,000, and more preferably 1/500 to 1/500,000. If the amount of the catalyst is too large, the removal of the catalyst becomes difficult which is often required. In contrast, if the amount of the catalyst is too small, the polymerization activity is often poor.

In the process for producing the cycloolefin addition polymer according to the present invention, the polymerization can be carried out in the presence or absence of a solvent by mixing together the above-mentioned catalyst with the monomer or monomers.

No limitation is imposed to the order in which the ingredient (A) for catalyst, the ingredients (B) to (D), and the monomer or monomers are mixed together for polymerization.

A solvent optionally used in the process for producing the cycloolefin addition polymer is not particularly limited provided that the polymerization is not influenced, but, commercially readily available solvents are preferably used. The solvent used can be chosen from those which are used for mixing the respective ingredients of the catalyst. Aromatic hydrocarbons, aliphatic hydrocarbons, alicyclic hydrocarbons, ethers and halogenated solvents are preferably used.

When the polymerization is carried out in a solvent, the concentration of the monomer or monomers is preferably in the range of 1 to 50% by weight, preferably 2 to 45% by weight and more preferably 5 to 40% by weight, based on the weight of a solution. When the monomer concentration is smaller than 1% by weight, the productivity is poor. In contrast, when the monomer concentration is larger than 50% by weight, the viscosity of the as-polymerized solution is too high and the solution is liable to be difficult to handle.

The polymerization temperature is not particularly limited, but is generally in the range of −30° C. to 200° C., preferably 0° C. to 180° C. The polymerization time is also not particularly limited, but is usually in the range of 1 minute to 100 hours.

The molecular weight of the cycloolefin addition polymer can be controlled by varying the ratio of the monomer or monomers to the catalyst and the polymerization temperature. The molecular weight thereof can also be controlled, for example, by adding hydrogen.

A cycloolefin addition polymer obtained by the production process according to the present invention has a weight average molecular weight (Mw) in the range of 10,000 to 1,000,000, preferably 20,000 to 800,000, as measured by gel permeation chromatography (GPC) and expressed in terms of that of polystyrene.

EXAMPLES

The invention will now be described specifically by the following examples that by no means limit the scope of the invention. Parts and % in the examples are by weight unless otherwise specified. The methods for test and evaluation adopted in the examples are as follows.

The degree of polymerization activity was evaluated by the ratio of the amount of polymer produced to a product of the mole number of catalyst with the polymerization time (that is expressed in unit "kg-polymer/(mol-Ti·h)".

(1) Identification of Transition Metal (A)

The transition metal (A) was determined by $^1$H-NMR analysis (chloroform D, room temperature), and X-ray crystal structure analysis.

(2) Weight Average Molecular Weight (Mw) and Number Average Molecular Weight (Wn) of Polymer Mw and Mn were measured by gel permeation chromatography (GPC) using tetrahydrofuran or chloroform as a solvent, and expressed in terms of that of polystyrene, (3) Copolymerization Ratio of Polymer Copolymerization analysis was determined by $^1$H-NMR analysis.

(4) Glass Transition Temperature (Tg).

Glass transition temperature (Tg) of polymer was measured by differential scanning calorimetry (DSC) at a temperature elevation rate of 10° C. per minute.

Example 1

Synthesis of Transition Metal Compound (A)

Synthesis of (t-butylamide)dimethyl-9-[octamethyloctahydrobenzofluorenyl]silanetitanium dimethyl (tetrahydrofuran) complex (Complex I)

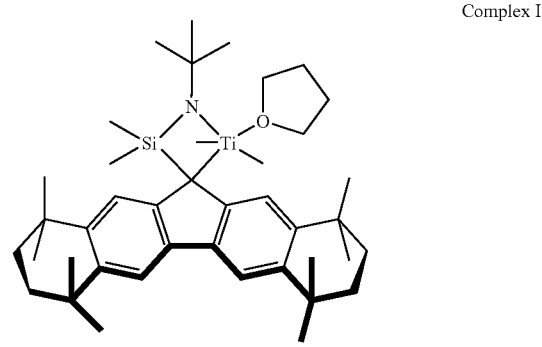

Complex I (t-butylamide)dimethyl-9-[octamethyloctahydrobenzofluorenyl]silane as a ligand was synthesized by the method described in Journal of the American Chemical Society, vol. 126, pp 16716-16717, 2004. 32 parts of the thus-synthesized ligand was placed in a glass reactor in a nitrogen gas atmosphere. To the content, 424 parts of diethyl ether was added, and the resultant solution was cooled to 20° C. To the solution, 8.06 parts of methyllithium was added, and the mixture was stirred at room temperature for 4 hours. The thus-obtained solution of a lithiated ligand in diethyl ether was incorporated in a previously prepared mixed liquid comprised of 7.60 parts of titanium tetrachloride and 130 parts of hexane at 0° C. The resultant mixture was stirred at room temperature overnight. The solvent was removed under a reduced pressure, and the obtained residue was extracted with tetrahydrofuran and hexane, and then subjected to decantation. A solvent was removed under a reduced pressure from the separated solution, the thus-obtained residue was extracted with diethyl ether. Then a procedure of decantation and filtration was repeated twice. Recrystallization of the solution gave 15.0 parts of a crystal of titanium complex I.

$^1$H-NMR spectrum of the titanium complex I is shown in FIG. 1 wherein "thf" means tetrahydrofuran. The $^1$H-NMR spectral characteristics of the titanium complex I were as follows.

$^1$H-NMR (CDCl$_3$) δppm: −0.34 (br, 6H), 0.75 (s, 6H), 1.22 (s, 9H), 1.36, 1.39, 1.40, 1.44 (s, 24H), 1.74 (s, 8H), 1.83 (br. 4H), 3.70 (br, 4H), 7.53 (s, 2H), 7.95 (s, 2H)

FIG. 2 is an illustration of X-ray structure analysis of the complex I (ORTEP). The distances between the titanium atom and each of the five carbon atoms on the cyclopentadienyl ring (which refers to a ring located in the center of octamethyloctahydrodibenzofluorenyl group) were as follows.

Ti—Cl: 2.198(6) Å, Ti-C2: 3.040(6) Å, Ti-C3: 3.884(6) Å, Ti-C4: 3.790(6) Å, Ti-C5: 2.851(6) Å

The above-mentioned X-ray structure analysis of complex I revealed that the Ti atom and the cyclopentadienyl ring are bonded in an $\eta^1$ mode.

Example 2

Polymerization of 2-Norbornene

A glass reactor was charged with 130 parts of toluene, 18.8 parts of norbornene and 4.64 parts of modified methylaluminoxane (MMAO-3A; available from Tosoh Finechem Corporation) dissolved in toluene. 0.13 part of the complex I dissolved in 8.67 parts of toluene was added to the content in the reactor. The oil bath in which the reactor was placed was heated to 50° C. whereby the polymerization was commenced. The content was stirred for 1 minute to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 9.70 parts of polymer. The polymerization activity was 2.910 kg-polymer/(mol-Ti·h). The Mw and Mn of polymer could not be measured by GPC using tetrahydrofuran or chloroform.

Example 3

Copolymerization of 2-Norbornene with 1-Hexene

A glass reactor was charged with 346 parts of toluene, 37.6 parts of norbornene, 8.40 parts of 1-hexene and 2.32 parts of modified methylaluminoxane (MMAO-3A; available from Tosoh Finechem Corporation) dissolved in toluene. 0.06 part of the complex I dissolved in 8.67 parts of toluene was added to the content in the reactor. The oil bath in which the reactor was placed was heated to 50° C. whereby the polymerization was commenced. The content was stirred for 5 minutes to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 13.7 parts of polymer. The polymerization activity was 1.644 kg-polymer/(mol-Ti·h). The Mw of polymer was 152,400 and the Mn of polymer was 89,200.

Example 4

Copolymerization of Dicyclopentadiene with Ethylene

A pressure-resistant glass reactor equipped with a stirrer was charged with 346 parts of toluene and 54.8 parts of dicyclopentadiene, and ethylene gas was blown into the reactor at room temperature. 4.64 parts of modified methylaluminoxane (MMAO-3A; available from Tosoh Finechem Corporation) dissolved in toluene was added to the content. Then, 0.13 part of the complex I dissolved in 8.67 parts of toluene was added to the content in the reactor. The oil bath in which the reactor was placed was heated to 50° C. whereby the polymerization was commenced. The content was stirred for 4 minutes to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 33.9 parts of polymer. The polymerization activity was 2,542 kg-polymer/(mol-Ti·h). The Mw of polymer was 269,200 and the Mn of polymer was 88,100. The copolymerization ratio by mole of dicyclopentadiene/ethylene was 54.4/45.6.

Example 5

Synthesis of Transition Metal Compound (A)

Synthesis of (t-butylamide)dimethyl-9-(fluorenyl)silanetitanium dimethyl(tetrahydrofuran)complex (Complex III)

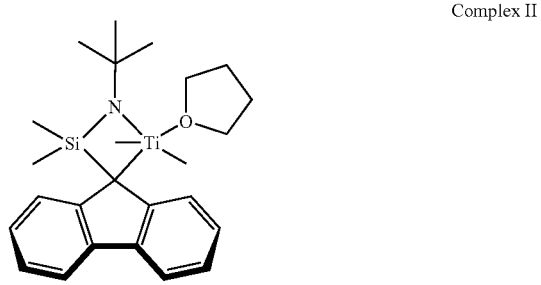

Complex II (t-butylamide)dimethyl-9-[fluorenyl]silane as a ligand was synthesized by the method described in Journal of the Organometallic Chemistry, vol. 691, pp 193-201, 2006. 24.3 parts of the thus-synthesized ligand was placed in a glass reactor in a nitrogen gas atmosphere. To the content, 424 parts of diethyl ether was added, and the resultant solution was cooled to −20° C. To the solution, 8.06 parts of methyllithium was added, and the mixture was stirred at room temperature for 4 hours. The thus-obtained solution of a lithiated ligand in diethyl ether was incorporated in a previously prepared mixed liquid comprised of 15.6 parts of titanium tetrachloride and 130 parts of hexane at 0° C. The resultant mixture was stirred at room temperature overnight. The solvent was removed under a reduced pressure, and the obtained residue was extracted with tetrahydrofuran and hexane, and then subjected to decantation. A solvent was removed under a reduced pressure from the separated solution, the thus-obtained residue was extracted with a mixed solvent of diethyl ether/hexane. Then a procedure of decantation and filtration was repeated twice. Recrystallization from hexane of the precipitate gave 12.0 parts of a crystal of titanium complex III.

Figure 3:
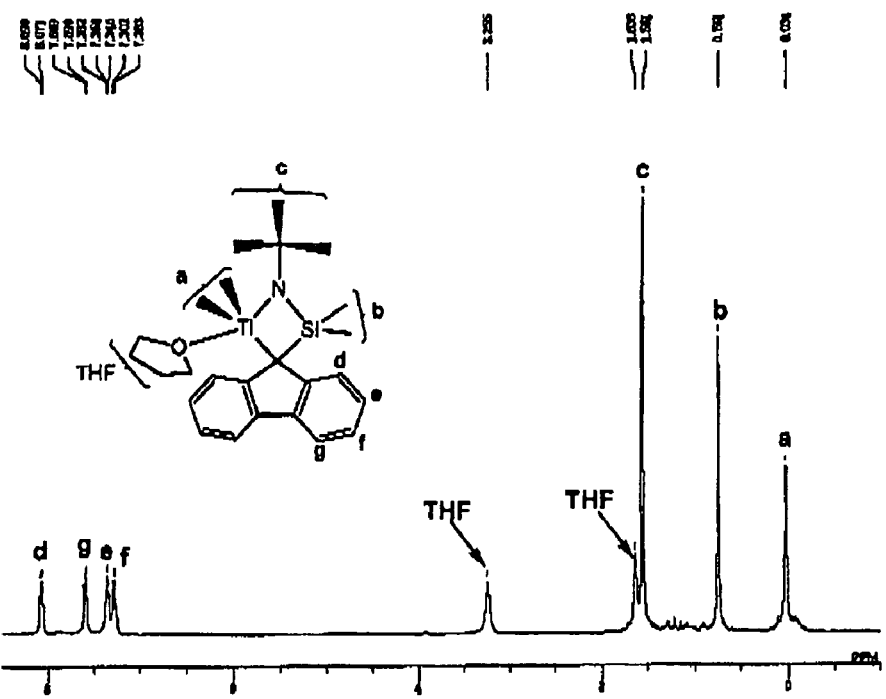
FIG. 3 is a $^1$H-NMR spectrum of complex III obtained in Example 5.

$^1$H-NMR spectrum of the titanium complex III is shown in FIG. 3 wherein "THF" means tetrahydrofuran. The $^1$H-NMR spectral characteristics of the titanium complex III were as follows.

$^1$H-NMR (CDCl$_3$) δ ppm: 0.03 (s, 6H), 0.76 (s, 6H), 1.56 (s, 9H), 1.64 (br, 4H), 3.26 (br, 4H), 7.28 (ddd, 2H), 7.36 (ddd, 2H), 7.59 (dd, 2H), 8.07 (dd, 2H)

Figure 4:
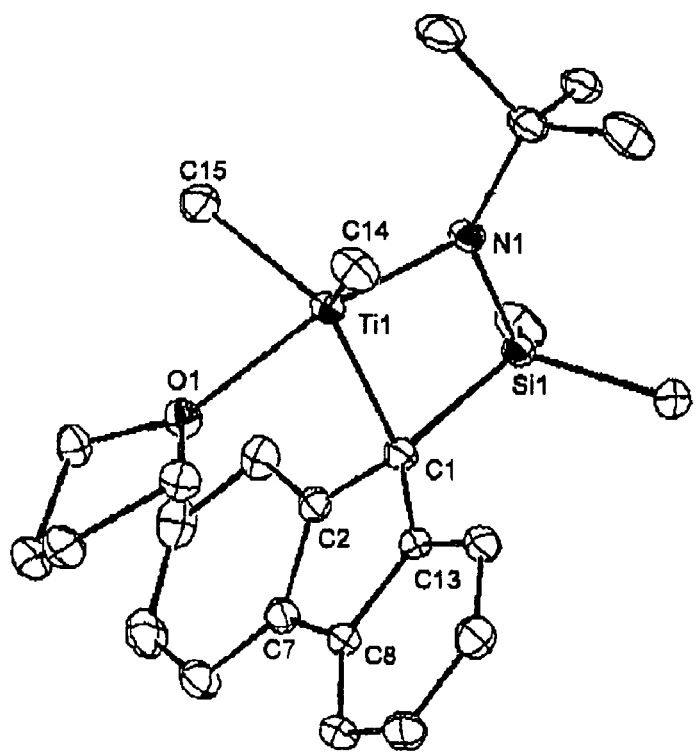
FIG. 4 is an illustration of X-ray structure analysis of complex III obtained in Example 5 (ORTEP [Oak Ridge Thermal Ellipsoid Plot]; hydrogen atoms are not shown).

FIG. 4 is an illustration of X-ray structure analysis of the complex III (ORTEP). The distances between the titanium atom and each of the five carbon atoms on the cyclopentadienyl ring were as follows.

Ti—Cl: 2.193(17) Å, Ti-C2: 3.065(16) Å, Ti-C3: 2.913 (17) Å, Ti-C7: 3.954(17) Å, Ti-C8: 3.875(17) Å

Example 6

Copolymerization of Dicyclopentadiene with Ethylene

A pressure-resistant glass reactor equipped with a stirrer was charged with 355 parts of toluene and 26.4 parts of dicyclopentadiene, and ethylene gas was blown into the reactor at room temperature. 4.90 parts of modified methylaluminoxane (MMAO-3A; available from Tosoh Finechem Corporation) dissolved in toluene was added to the content. Then, 8.87×10$^{-2}$ part of the complex III dissolved in 8.67 parts of toluene was added to the content in the reactor. The oil bath in which the reactor was placed was heated to 50° C. whereby the polymerization was commenced. The content was stirred for 3 minutes to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 35.1 parts of polymer. The polymerization activity was 3.510 kg-polymer/(mol-Ti·h). The Mw of polymer was 121,300 and the Mn of polymer was 18,600. The copolymerization ratio by mole of dicyclopentadiene/ethylene was 40.6/59.4. Tg was 142° C.

Example 7

Copolymerization of Dicyclopentadiene with Ethylene

A pressure-resistant glass reactor equipped with a stirrer was charged with 355 parts of toluene and 52.8 parts of dicyclopentadiene, and ethylene gas was blown into the reactor under an atmospheric pressure. 4.90 parts of modified methylaluminoxane (MMAO-3A; available from Tosoh Finechem Corporation) dissolved in toluene was added to the content. Then, 8.87×10$^{-2}$ part of the complex III dissolved in 8.67 parts of toluene was added to the content in the reactor. The oil bath in which the reactor was placed was heated to 50° C. whereby the polymerization was commenced. The content was stirred for 3 minutes to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 35.2 parts of polymer. The polymerization activity was 3.520 kg-polymer/(mol-Ti·h). The Mw of polymer was 272,100 and the Mn of polymer was 35,900. The copolymerization ratio by mole of dicyclopentadiene/ethylene was 53.3/46.7. Tg was 193° C.

Comparative Example 1

Polymerization of 2-Norbornene

Polymerization of 2-norbornene was carried out using (t-butylamide)dimethyl-9-fluorenylsilanetitanium dimethyl complex (Complex II) as a group 4 transition metal compound.

In this compound having the following formula, a Ti atom is bonded to a cyclopentadienyl ring (the central ring in the fluorenyl group) in an .eta.sup.3 mode, and therefore the neutral Lewis base (L) is not coordinated to the Ti atom.

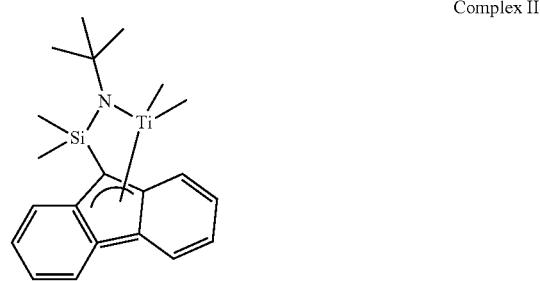

Complex II

A glass reactor was charged with 260 parts of toluene, 37.6 parts of norbornene and 37.1 parts of modified methylaluminoxane (MMAO-3A; available from Tosoh Finechem Corporation) dissolved in toluene. 0.07 part of the complex II dissolved in 8.67 parts of toluene was added to the content in the reactor. The oil bath in which the reactor was placed was heated to 50° C. whereby the polymerization was commenced. The content was stirred for 30 minutes to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 19.7 parts of polymer. The polymerization activity was 197 kg-polymer/(mol-Ti·h). The Mw and Mn of polymer could not be measured by GPC using tetrahydrofuran or chloroform.

Comparative Example 2

Copolymerization of 2-Norbornene with 1-Hexene

A glass reactor was charged with 260 parts of toluene, 18.8 parts of norbornene, 16.8 parts of 1-hexene and 37.1 parts of modified methylaluminoxane (MMAO-3A; available from Tosoh Finechem Corporation) dissolved in toluene. 0.07 part of the complex II dissolved in 8.67 parts of toluene was added to the content in the reactor. The oil bath in which the reactor was placed was heated to 50° C. whereby the polymerization was commenced. The content was stirred for 60 minutes to carry out the polymerization, and then the polymerization liquid was poured into a large amount of methanol acidified with hydrochloric acid to completely precipitate a polymer. The polymer precipitate was separated by filtration, and washed. Then the washed polymer was dried under reduced pressure at 80° C. for 15 hours to give 8.40 parts of polymer. The polymerization activity was 42 kg-polymer/(mol-Ti·h). The Mw of polymer was 49,900 and the Mn of polymer was 33,100.

When the complex II not having a neutral Lewis base coordinated, which is different from the transition metal compound (A), was used, the polymerization activity for homopolymerization of cycloolefin and that for copolymerization of cycloolefin with 1-hexene were low (Comparative Examples 1 and 2).

In contrast, when the complexes I and III which are the transition metal compound (A) according to the present invention are used, high polymerization activity was exhibited for both of the addition polymerization of cycloolefin (Example 2) and the addition copolymerization of cycloolefin with α-olefin (Examples 3, 4, 6 and 7).

The invention claimed is:

1. A process for producing a cycloolefin addition polymer comprising addition-polymerizing a cycloolefin in the presence of a catalyst comprising a combination of (A) a transition metal compound of Group 4 of the Periodic Table, represented by the following general formula (1), with (B) an organoaluminum oxy compound, and/or (C) a compound capable of reacting with the Group 4 transition metal compound (A) to form an ion pair,

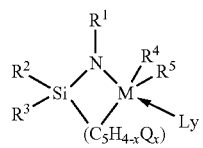

(1)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $C_5H_{4-x}Q_x$ refers to a cyclopentadienyl ring having "x" number of substituents Q, where x is an integer of 1 to 4, and each Q independently represents a $C_1$-$C_{20}$ hydrocarbon group which may have a halogen atom or atoms as a substituted, or a silyl group which may have a $C_1$-$C_{12}$ hydrocarbon group or groups as a substituent; wherein two adjacent Qs in the $C_5H_{4-x}Q_x$ may be bonded, together with the carbon atoms to which the two Qs are attached, to form a cyclic moiety having 4 to 20 carbon atoms whereby the $C_5H_{4-x}Q_x$ is rendered a polycyclic cyclopentadienyl ring; L is a neutral Lewis base, and y is an integer of 1 or 2.

2. The process for producing a cycloolefin addition polymer according to claim 1, wherein, in the general formula (1), the $C_5H_{4-x}Q_x$ is bonded to M in an $\eta^1$ mode.

3. The process for producing a cycloolefin addition polymer according to claim 1, wherein, in the general formula (1), the $C_5H_{4-x}Q_x$ is a fluorenyl group or a substituted fluorenyl group.

4. The process for producing a cycloolefin addition polymer according to claim 1, wherein the Group 4 transition metal compound (A) is represented by the following general formula (3):

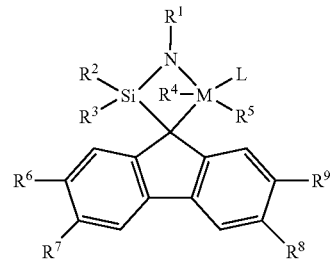

(3)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $R^6$ to $R^9$ each independently represent a hydrogen atom, a $C_1$-$C_{12}$ alkyl group, a $C_5$-$C_{12}$ cycloalkyl group, a $C_6$-$C_{12}$ aryl group or a halogen atom, or a $C_1$-$C_{12}$ hydrocarbon group which may have a halogen atom or atoms as a substituent, or a silyl group which may have a $C_1$-$C_{12}$ hydrocarbon group or groups as a substituent; $R^6$ and $R^7$, and $R^8$ and $R^9$ may be bonded together to form a ring; and L is a neutral Lewis base.

5. A catalyst for addition-polymerization of a cycloolefin comprising a combination of (A) a transition metal compound of Group 4 of the Periodic Table, represented by the following general formula (1), with (B) an organoaluminum oxy compound, and/or (C) a compound capable of reacting with the Group 4 transition metal compound (A) to form an ion pair,

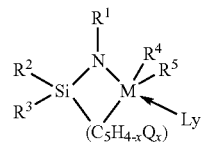

(1)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$, aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $C_5H_{4-x}Q_x$ refers to a cyclopentadienyl ring having "x" number of substituents Q, where x is an integer of 1 to 4, and each Q independently represents a $C_1$-$C_{20}$ hydrocarbon group which may have a halogen atom or atoms as a substituted, or a silyl group which may have a $C_1$-$C_{12}$ hydrocarbon group or groups as a substituent; wherein two adjacent Qs in the $C_5H_{4-x}Q_x$ may be bonded, together with the carbon atoms to which the two Qs are attached, to form a cyclic moiety having 4 to 20 carbon atoms whereby the $C_5H_{4-x}Q_x$ is rendered a polycyclic cyclopentadienyl ring; L is a neutral Lewis base, and y is an integer of 1 or 2.

6. The catalyst for addition-polymerization of a cycloolefin according to claim 5, wherein, in the general formula (1), the $C_5H_{4-x}Q_x$ is bonded to M in an $\eta^1$ mode.

7. The catalyst for addition-polymerization of a cycloolefin according to claim 5, wherein, in the general formula (1), the $C_5H_{4-x}Q_x$ is a fluorenyl group or a substituted fluorenyl group.

8. The catalyst for addition-polymerization of a cycloolefin according to claim 5, wherein the Group 4 transition metal compound (A) is represented by the following general formula (3):

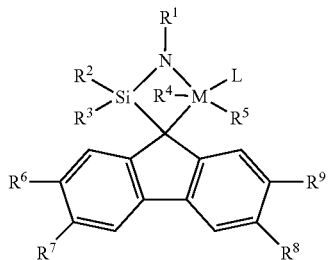

(3)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $R^6$ to $R^9$ each independently represent a hydrogen atom, a $C_1$-$C_{12}$ alkyl group, a $C_5$-$C_{12}$ cycloalkyl group, a $C_6$-$C_{12}$ aryl group or a halogen atom, or a $C_1$-$C_{12}$ hydrocarbon group which may have a halogen atom or atoms as a substituted, or a silyl group which may have a $C_1$-$C_{12}$ hydrocarbon group or groups as a substituent; $R^9$ and $R^7$, and $R^5$ and $R^9$ may be bonded together to form a ring; and L is a neutral Lewis base.

9. The catalyst for addition-polymerization of a cycloolefin according to claim 5, wherein the Group 4 transition metal compound (A) is a titanium compound represented by the following general formula (2):

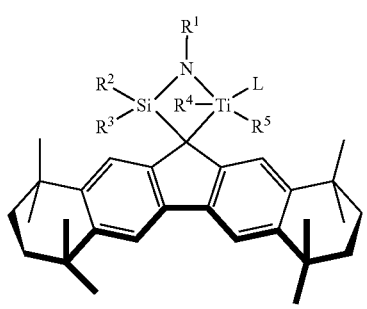

(2)

wherein $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; and L is a neutral Lewis base.

10. A transition metal compound of Group 4 of the Periodic Table, represented by the following general formula (3):

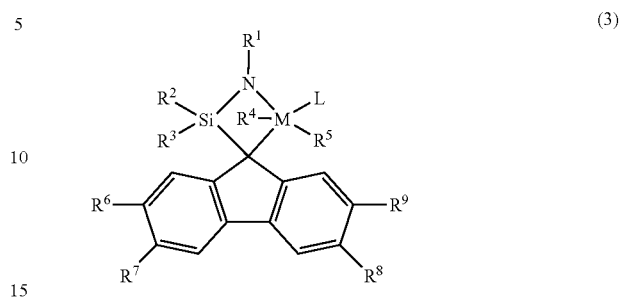

(3)

wherein M represents a transition metal atom of Group 4 of the Periodic Table; $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; $R^6$ to $R^9$ each independently represent a hydrogen atom, a $C_1$-$C_{12}$ alkyl group, a $C_5$-$C_{12}$ cycloalkyl group, a $C_6$-$C_{12}$ aryl group or a halogen atom, or a $C_1$-$C_{12}$ hydrocarbon group which may have a halogen atom or atoms as a substituted, or a silyl group which may have a $C_1$-$C_{12}$ hydrocarbon group or groups as a substituent, provided that, in the case when M is titanium, $R^6$ and $R^7$, and/or $R^8$ and $R^9$ may be bonded together to form a ring; and L is a neutral Lewis base.

11. The Group 4 transition metal compound according to claim 10, which is a titanium compound represented by the following general formula (2):

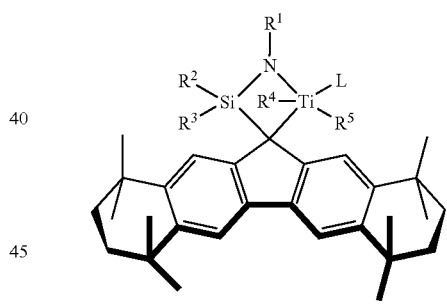

(2)

wherein $R^1$ to $R^3$ each independently represent a hydrogen atom, a $C_1$-$C_{12}$ alkyl group, a $C_5$-$C_{12}$ cycloalkyl group or a $C_6$-$C_{12}$ aryl group; $R^4$ and $R^5$ each independently represent a hydrogen atom, a $C_1$-$C_{12}$ alkyl group, a $C_5$-$C_{12}$ cycloalkyl group, a $C_6$-$C_{12}$ aryl group or a halogen atom; and L is a neutral Lewis base.

* * * * *

UNITED STATES PATENT AND TRADEMARK OFFICE
CERTIFICATE OF CORRECTION

| | | |
|---|---|---|
| PATENT NO. | : 7,868,107 B2 | Page 1 of 1 |
| APPLICATION NO. | : 12/073704 | |
| DATED | : January 11, 2011 | |
| INVENTOR(S) | : Kei Nishii et al. | |

It is certified that error appears in the above-identified patent and that said Letters Patent is hereby corrected as shown below:

Column 6, line numbered 20, change "AS" to --As--.

Column 8, line numbered 54, change "1/0.100," to --1/100--.

Column 13, line numbered 49, change "2.910" to --2,910--.

Column 14, line numbered 4, change "1.644" to --1,644--.

Column 14, line numbered 43, change "Complex II" to --Complex III--.

Column 15, line numbered 45, change "3.510" to --3,510--.

Column 16, line numbered 5, change "3.520" to --3,520--.

Claim 8, $2^{nd}$ line from the bottom (at column 19, line numbered 30), change "$R^9$ and $R^7$, and $R^5$ and $R^9$" to --$R^6$ and $R^7$, and $R^8$ and $R^9$--.

Signed and Sealed this
Tenth Day of May, 2011

David J. Kappos
*Director of the United States Patent and Trademark Office*